US008998820B2

(12) United States Patent
Jarverud et al.

(10) Patent No.: US 8,998,820 B2
(45) Date of Patent: Apr. 7, 2015

(54) DEVICES AND METHOD FOR DETERMINING AND MONITORING A CARDIAC STATUS OF A PATIENT BY USING PLVDT OR PLVST PARAMETERS

(75) Inventors: Karin Jarverud, Solna (SE); Anders Bjorling, Solna (SE); Jay Snell, Studio City, CA (US)

(73) Assignee: St. Jude Medical AB, Jarfalla (SE)

( * ) Notice: Subject to any disclaimer, the term of this patent is extended or adjusted under 35 U.S.C. 154(b) by 135 days.

(21) Appl. No.: 13/392,395

(22) PCT Filed: Aug. 27, 2009

(86) PCT No.: PCT/SE2009/000393
§ 371 (c)(1),
(2), (4) Date: Feb. 24, 2012

(87) PCT Pub. No.: WO2011/025415
PCT Pub. Date: Mar. 3, 2011

(65) Prior Publication Data
US 2012/0157861 A1 Jun. 21, 2012

(51) Int. Cl.
*A61B 5/02* (2006.01)
*A61B 5/0452* (2006.01)
*A61B 5/11* (2006.01)
*A61B 5/00* (2006.01)
*A61N 1/362* (2006.01)

(52) U.S. Cl.
CPC ............ *A61B 5/0452* (2013.01); *A61B 5/02* (2013.01); *A61B 5/1118* (2013.01); *A61B 5/6846* (2013.01); *A61N 1/3627* (2013.01)

(58) Field of Classification Search
CPC ........ A61B 5/02; A61B 5/0205; A61B 5/026; A61B 5/145; A61B 5/1455
See application file for complete search history.

(56) References Cited

U.S. PATENT DOCUMENTS

| | | | |
|---|---|---|---|
| 5,447,523 | A | 9/1995 | Schaldach |
| 6,064,910 | A | 5/2000 | Andersson et al. |
| 6,792,308 | B2 | 9/2004 | Corbucci |
| 6,886,411 | B2 | 5/2005 | Kjellman et al. |
| 7,447,533 | B1 | 11/2008 | Fang et al. |

(Continued)

OTHER PUBLICATIONS

Bombardini, Tonino et al., "Diastolic time—frequency relation in the stress echo lab: filling timing and flow at different heart rates," Cardiovascular Ultrasound. 2008;6:15 http://www.cardiovascularultrasound.com/content/6/1/15.

(Continued)

*Primary Examiner* — Christopher D Koharski
*Assistant Examiner* — Elizabeth K So

(57) ABSTRACT

The present invention relates to an improved medical device and method for accurately and reliably determining a cardiac status of a patient. An implantable medical device, IMD, comprises a sensor arrangement adapted to sense signals related to mechanical activity of the heart and an activity level sensor arrangement adapted to sense an activity level of the patient. Further, the IMD calculates a percentage of left ventricular diastolic time (PLVDT) for a cardiac cycle corresponding to a relation between a diastolic time interval and a cardiac cycle time interval using the determined systolic and diastolic time intervals or a percentage of left ventricular systolic time (PLVST) for a cardiac cycle corresponding to a relation between a systolic interval time interval and a cardiac cycle time interval. A cardiac status is determined based on the calculated PLVDT (or PLVST) and on an activity level of the patient.

8 Claims, 8 Drawing Sheets

(56) References Cited

U.S. PATENT DOCUMENTS

| | | | |
|---|---|---|---|
| 2004/0116969 A1* | 6/2004 | Owen et al. | 607/6 |
| 2006/0106322 A1* | 5/2006 | Arand et al. | 600/514 |
| 2007/0038137 A1 | 2/2007 | Arand et al. | |
| 2007/0191725 A1 | 8/2007 | Nelson | |
| 2007/0299356 A1* | 12/2007 | Wariar et al. | 600/513 |
| 2008/0091239 A1 | 4/2008 | Johansson et al. | |
| 2008/0287818 A1* | 11/2008 | Shelchuk et al. | 600/509 |
| 2009/0062667 A1 | 3/2009 | Fayram et al. | |
| 2009/0204165 A1 | 8/2009 | Bauer | |

OTHER PUBLICATIONS

International Search Report—Int'l App. No. PCT/SE2009/000393; Int'l Filing Date: Aug. 27, 2009.

Written Opinion of the Int'l Searching Authority—Int'l App. No. PCT/SE2009/000393; Int'l Filing Date: Aug. 27, 2009.

\* cited by examiner

DEVICES AND METHOD FOR DETERMINING AND MONITORING A CARDIAC STATUS OF A PATIENT BY USING PLVDT OR PLVST PARAMETERS

TECHNICAL FIELD

The present invention generally relates to implantable medical devices, such as pacemakers, and, in particular, to techniques for determining and monitoring a cardiac status of a patient.

BACKGROUND OF THE INVENTION

The cardiac cycle has two phases; diastole and systole. During the systolic phase, the heart ejects blood through a pumping action requiring energy. During the diastolic phase, the heart repolarizes electrically, relaxes mechanically and is refilled with blood. In addition, the oxygen needed for the heart to perform its systolic activity is delivered to the heart during diastole. If the diastolic phase is disturbed or shortened in time, the performance during systole is compromised.

In "Diastolic time—frequency relation in the stress echo lab: filling timing and flow at different heart rates", by Bombardini T. et al., Cardiovascular Ultrasound, 2008 Apr. 21; 6:15, the diastolic and systolic time intervals were studied in normal persons, i.e. persons that do not suffer from cardiac related problems, and in patients suffering from stress induced ischemia and severe mitral regurgitation. The time intervals were measured by means of echocardiography. In particular, the different persons were studied during rest and stress. It was found that, in normal persons, the length of the diastolic time interval approached the length of the systolic time interval during exercise at high heart rates, i.e. heart rates above about 150-160 bpm. For lower heart rates the diastolic time interval was found to be significantly longer than the systolic time interval. Further, during rest, the diastolic time interval was found to be significantly longer than the systolic time interval. On the other hand, for patients suffering from stress induced ischemia and severe mitral regurgitation, the diastolic time interval was found to be substantially equal to, or even shorter than, the systolic time interval at both low and high heart rates.

Thus, the length of the diastolic phase or diastolic time interval of the cardiac cycle seems to be an important parameter which contains valuable information of the cardiac status of a patient. Further, the diastolic time interval and the ratio between the diastolic time interval and the systolic time interval seem to be important and valuable measures for determining a cardiac status of a patient.

There exist a large number of different solutions in which these parameters are utilized for e.g. controlling the functioning of a pacemaker and/or for determining a cardiac status of a patient.

For example, in U.S. Pat. No. 6,792,308 to Corbucci, a cardiac pacemaker for evaluating myocardial performance using information of the diastolic and systolic intervals is disclosed. In particular, the myocardial performance is assessed by determining a QT interval based on electrogram (EGM) readings and by detecting first and second heart sounds (S1 and S2). The QT interval and the timing of the first and second heart sounds is used to evaluate certain parameters related to myocardial performance. Such parameters include a S1S2 interval which is the difference between, on one hand, the interval between the Q-wave and the onset of the first heart sound S1, and, on the other hand, the interval between the Q-wave and the onset of the second heart sound S2. The S1S2 interval serves as an estimate of the systolic interval or the ejection time (ET). Another parameter is the S2S1 interval which is an estimate of the diastolic interval or the filling time (FT). These intervals are used to determine a ratio of the systolic interval to the diastolic interval, which ratio indicates a systolic/diastolic balance. According to U.S. Pat. No. 6,792,308, this ratio is used to evaluate the upper rate limit in paced patients and for evaluating the rate limit for patients with rate dependent angina.

Yet, there is a need within the art of improved medical devices and methods for determining a cardiac status of a patient.

SUMMARY OF THE INVENTION

The present invention provides according to an object an improved medical device and method for determining a cardiac status of a patient.

According to another object of the present invention, there is provided an improved medical device and method for accurately and reliably determining a cardiac status of a patient.

According to a further object of the present invention, there is provided a medical device and method capable of determining a cardiac status of patient with an improved specificity.

These and other objects of the present invention are achieved by means of a method and an implantable medical device having the features defined in the independent claims. Embodiments of the invention are characterized by the dependent claims.

According to a first aspect of the present invention, there is provided an implantable medical device, IMD, for determining a cardiac status of a patient, the medical device being connectable to at least one medical lead for contact with tissue of a heart of the patient. The IMD comprises a sensor arrangement adapted to sense signals related to mechanical activity of the heart and an activity level sensor arrangement adapted to sense an activity level of the patient. Further, the IMD includes a cardiac event identifying module adapted to identify predetermined cardiac events in the cardiac signals and to determine a systolic time interval and a diastolic time interval of a cardiac cycle using the identified cardiac events, a calculation module adapted to calculate a percentage of left ventricular diastolic time (PLVDT) for a cardiac cycle corresponding to a relation between a diastolic time interval and a cardiac cycle time interval using the determined systolic and diastolic time intervals or a percentage of left ventricular systolic time (PLVST) for a cardiac cycle corresponding to a relation between a systolic interval time interval and a cardiac cycle time interval using the determined systolic and diastolic time intervals, and a cardiac status determining module adapted to synchronize the activity level with the calculated PLVDT (or PLVST) over time, i.e. to secure that a certain activity level of the patient at a certain point of time is synchronized to the PLVDT (or PLVST) for the same point of time in order to allow, for example, a display of the PLVDT (or PLVST) and the activity level as a function of time, and to determine a cardiac status based on the calculated PLVDT (or PLVST) and on the activity level.

According to a second aspect of the present invention, there is provided a method for determining a cardiac status of a patient in an implantable medical device being connectable to at least one medical lead for contact with tissue of a heart of the patient. The method comprises the steps of: sensing signals related to mechanical activity of the heart, sensing an activity level of the patient, identifying predetermined cardiac events in the cardiac signals and determining a systolic time interval and a diastolic time interval of a cardiac cycle using the identified cardiac events, calculating a percentage of left ventricular diastolic time (PLVDT) for a cardiac cycle corresponding to a relation between a diastolic time interval and a cardiac cycle time interval using the determined systolic and diastolic time intervals or a percentage of left ventricular systolic time (PLVST) for a cardiac cycle corresponding to a relation between a systolic interval time interval and a cardiac cycle time interval using the determined systolic and diastolic time intervals, synchronizing the activity level with the calculated PLVDT (or PLVST) over time i.e. to secure that a certain activity level of the patient at a certain point of time is synchronized to the PLVDT (or PLVST) for the same point of time in order to allow, for example, a display of the PLVDT (or PLVST) and the activity level as a function of time, and determining a cardiac status based on the calculated PLVDT (or PLVST) and on the activity level.

In embodiments of the present invention, the signals acquired reflecting the mechanical activity of the heart may include intracardiac pressure signals, intracardiac impedance signals, photoplethysmographic signals, and/or heart sound signals.

The present invention is based on the insight that a metric or measure including a percentage of left ventricular diastolic time to total cardiac cycle time (PLVDT=percentage of left ventricular diastolic time) contains valuable information of the cardiac status of a patient. This metric provides an accurate and reliable measure on how much of the cardiac work that is put in the diastolic phase. The higher the PLVDT metric within predetermined limits and for given situation, the better cardiac status of the patient will be. If the PLVDT metric is reduced to a certain level, the cardiac oxygen supply is in jeopardy. The PLVDT is defined as LVDT (left ventricular diastolic time)/cardiac cycle time, i.e. the percentage of the left ventriclar diastolic time of the total cardiac cycle time, or

PLVDT=LVDT/(LVDT+LVST), where LVST is Left Ventricular Systolic Time. The inventors have found that a range for the PLVDT metric that signals a good cardiac status may vary between different patients. However, a PLVDT (or PLVST) exceeding an upper limit or being below a lower limit of such patient specific range is an indication of an impaired cardiac status. For example, a patient specific range may be between 55% and 65%. In this case, If the PLVDT is lower than 55%, it might be an indication of restrictive filling patterns or of the occurrence of an elevated left ventricular end diastolic pressure. On the other hand, a PLVDT metric that exceeds 65% may be an indication of hypovolemia. Thus, this metric focuses on the diastolic portion of the cardiac cycle and its relation to the total cardiac cycle. PLVDT reflects both the patient's risk to develop ischemia and the HF status and provides an objective measure of these aspects of the patient's health status. However, even though PLVDT itself may provide an accurate basis for a determination of a cardiac status of a patient, at least for some patients, the inventors have found that the accuracy and specificity of the status determination can be significantly improved by taking further parameters into account in the status determination. Studies have shown that the activity level of the patient has a considerably impact on the conclusions that can be drawn from a certain level of the PLVDT (or PLVST) or a certain development of the PLVDT (or PLVST). For example, a period of slowly decreasing PLVDT synchronized with a slowly decreasing activity level may be an indication of an exacerbation of heart failure. Further, a decreasing PLVDT occurring at a stable activity level may be an indication of that the cardiac status is impaired and the patient may be advised to visit the care giver for a check-up. Thus, since the heart is unable to perfuse itself at a too short diastole, i.e. a too low PLVDT, the risk of ischemia increases as PLVDT decreases. Furthermore, an increased ventricular asynchrony would lead to a decrease in PLVDT as well as to an exacerbation of the patient's heart failure. Also, since heart failure patients are unable to increase their stroke volume as much as healthy individuals and thereby increase their rate and cardiac output to a higher degree at even moderate exercise, and since ischemia (both silent and non-silent) often make their debut at physical activity, trending the PLVDT in combination with the output from the activity sensor provides very important information regarding the cardiac status of the patient. To even further improve the specificity and accuracy of the status determination, the heart rate may also be synchronized with the activity level and PLVDT or PLVST. For example, in some situations the heart rate will increase if PLVDT (or PLVST) decreases (or increases) due to an impairment of the heart failure status in order to secure the blood circulation.

The PLVDT (or PLVST), the activity level and/or the heart rate as a function of time displayed on a programmer can be a very useful diagnostic tool for the medical doctor when determining a cardiac status of a patient in accordance with the discussion above. For example, a regular follow-up visit by the patient, or at a visit by the patient caused by an impairment of the experienced state of health, the medical doctor can use PLVDT (or PLVST) displayed simultaneously with the activity level and the heart rate on a programmer to determine a cardiac status. Thus, by studying the displayed graphs over time of the PLVDT (or PLVST), activity level and/or the heart rate and the trends over time, the doctor can, for example, determine whether a patient suffering from heart failure is getting worse or not. For example, a period of slowly decreasing PLVDT synchronized with a slowly decreasing activity level may be an indication of an exacerbation of heart failure.

In embodiments of the present invention, the implantable medical device may store the PLVDT (or PLVST), activity level and heart rate output over time in its memory, for example, in a control module. This trend may be used in the status determination at the hospital and can also be transmitted via a communication unit to, for example, a clinic to be viewed by the physician at the next follow-up as discussed above.

In embodiments of the present invention, a rate of change (derivative) of PLVDT or PLVST is calculated and that rate of change also provides useful information in the status determination. For example, a gradually increasing PLVDT (or decreasing PLVST) over time synchronized with a stable or gradually decreasing activity level is determined to be an indication of a impaired cardiac status. Similarly, a gradually decreasing PLVDT (or increasing PLVST) over time synchronized with a stable or gradually decreasing activity level may also be determined to be an indication of a impaired cardiac status. Consequently, a decreasing or increasing PLVDT (or PLVST) is an indication of an impairment of the cardiac status. However, the starting point must also be considered when determining the cardiac status as well as the activity level and/or heart rate. For example, a rather significant increase or decrease of the PLVDT (or PLVST) from a predetermined level within a predetermined range at a specific activity level and/or heart rate for a specific patient may not be any indication (or a weak indication) of an imparied cardiac status, while a rather small increase or decrease from a level at a limit of the predetermined range for that specific patient may be a strong indication of an impaired cardiac status.

According to an embodiment of the present invention, a prognosis based on a present rate of change of PLVDT (or PLVST) is determined. For example, the present rate of change is extrapolated and a future point of time when a lower or higher limit of a predetermined range of the PLVDT (or PLVST), which may be patient specific e.g. within 55%-65% (or 35%-45% for PLVST) at a specific activity level and/or heart rate or a range of activity levels and/or heart rates, is crossed can be calculated. The patient may, for example, be alerted that a worsening of the heart failure status can be expected within a certain period of time. Thus, this gives the patient time to take measures or precautions to avoid the potential event.

Furthermore, the implantable medical device may include an alarm function, which may initiate an alarm based on the PLVDT and/or the status determination. For example, if a PLVDT being outside a predetermined range, which may be patient specific e.g. a range of 55%-65%, has been observed for a period of time at certain activity level and/or heart rate, the implantable medical device may issue a warning to the patient instructing him or her to get in contact with the hospital or clinic. The warning may be a message to a home monitoring unit in the patient's home transmitted wirelessly from the IMD, or a vibration of a vibrating unit in the IMD. The warning may also, or instead, be transmitted to the clinic instructing the physician to get in contact with the patient. For example, clinical experience has shown that a too low PLVDT may in some cases predict future VF (ventricular fibrillation). Thus, at a very low PLVDT, it may be time critical to get the patient to the hospital.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

BRIEF DESCRIPTION OF THE DRAWINGS

Exemplifying embodiments of the invention will be described below with reference to the accompanying drawings, in which.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention. Thus, even though particular types of implantable medical devices such as heart stimulators will be described, e.g. biventricular pacemakers, the invention is also applicable to other types of cardiac stimulators such as dual chamber stimulators, implantable cardioverter defibrillators (ICDs), etc.

Figure 1:
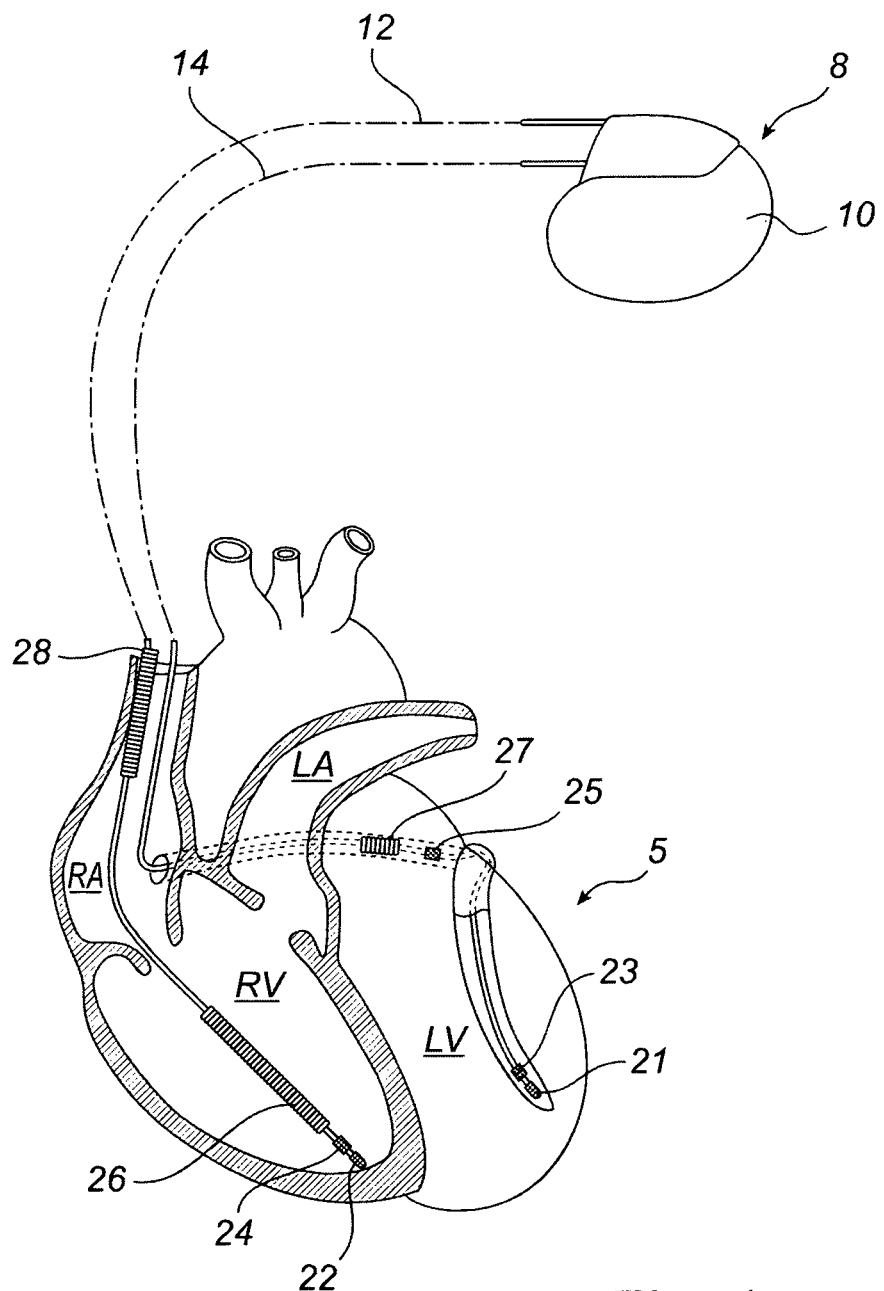
FIG. 1 is a simplified, partly cutaway view, illustrating an implantable medical device according to the present invention with a set of leads implanted into the heart of a patient.

Turning now to FIG. 1, which is a simplified schematic view of one embodiment of an implantable medical device ("IMD") 8 according to the present invention. IMD 8 has a hermetically sealed and biologically inert case 10. In this embodiment, IMD 8 is a pacemaker which is connectable to pacing and sensing leads 12, 14, in this illustrated case two leads. However, as the skilled person understands, the pacemaker may also be connected to one or several, e.g. three or more, pacing and sensing leads. IMD 8 is in electrical communication with a patient's heart 5 by way of a right ventricular lead 12 having a right ventricular (RV) tip electrode 22, a RV ring electrode 24, RV coil electrode 26, and a superior vena cava (SVC) coil electrode 28. Typically, the RV lead is transvenously inserted into the heart 5 so as to place the RV coil electrode 26 in the right ventricular apex and the SVC coil electrode 28 in the superior vena cava. Accordingly, the right ventricular lead 12 is capable of receiving cardiac signals, and delivering stimulation in the form of pacing to the right ventricle RV.

In order to sense left atrial and ventricular cardiac signals and to provide left chamber pacing therapy, IMD 8 is coupled to a "coronary sinus" lead 14 designed for placement in the coronary sinus region via the coronary sinus for positioning a distal electrode adjacent to the left atrium. As used herein, the wording "coronary sinus region" refers to the vasculature of the left ventricle, including any portion of the coronary sinus, great cardiac vein, left marginal vein, middle cardiac vein, and/or small cardiac vein or any other cardiac vein accessible via the coronary sinus. Accordingly, the coronary sinus lead 14 is designed to receive atrial and ventricular pacing signals and to deliver left ventricular pacing therapy using at least a left ventricular (LV) tip electrode 21, a LV ring electrode 23 left atrial pacing therapy using at least a LA electrode 25 and a LA electrode 27.

Figure 2:
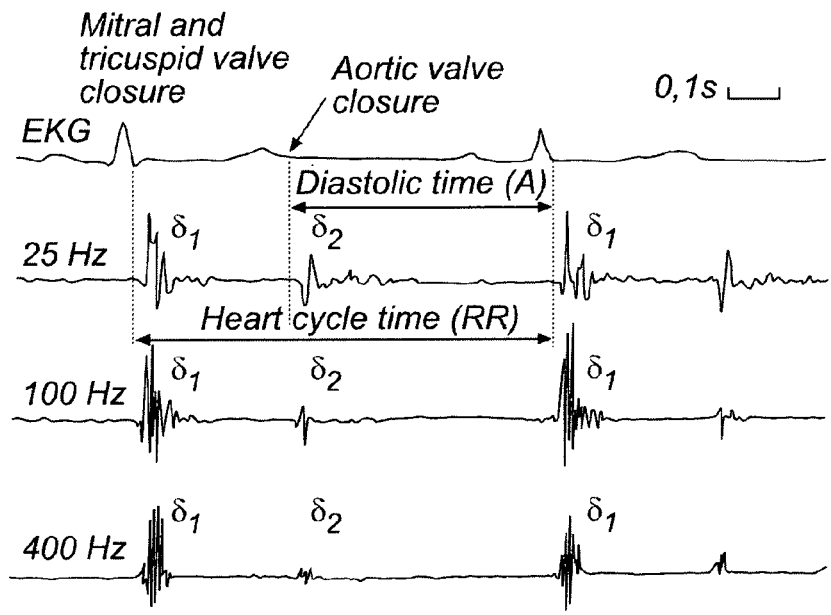
FIG. 2 schematically illustrates a heart sound waveform, where the time of mitral and tricuspid valves is marked, i.e. corresponding to the first heart sound S1, and the closure of the aortic valve, i.e. corresponding to the second heart sound S2, is marked.

With this configuration bi-ventricular therapy can be performed. Although only two medical leads are shown in FIG. 2, it should also be understood that additional stimulation leads (with one or more pacing, sensing, and/or shocking electrodes) may be used in order to efficiently and effectively provide pacing stimulation to the left side of the heart or atrial cardioversion. For example, a right atrium (RA) lead implanted in the atrial appendage having a RA tip electrode and a RA ring electrode may be arranged to provide electrical communication between the right atrium (RA) and the IMD 8.

IMD 8 is an exemplary device that may use the techniques according to the invention. The invention is not limited to the device shown in FIG. 1. For example, while the pacemaker 8 is depicted as a three-chamber pacemaker, the invention can also be practiced in a single-chamber, dual-chamber, or four-chamber pacemaker. According to various embodiments of the present invention, IMD 8 detects electrical cardiac signals, including e.g. the T-wave and the R-wave.

According to an embodiment of the present invention, first and second heart sounds S1 and S2, respectively, are detected, either by the IMD 8 or by a sensor (not shown in FIG. 1) external to the IMD 8 and connected to a programmer. The heart sounds may be detected using, for example, a microphone, an accelerometer, a pietzoelectric sensor, or a vibration sensor. In a preferred embodiment, the heart sounds are detected by means of a microphone, which detects the distinct sound arising from the closure of the tricuspid and mitral valves, i.e. the first heart sound S1, and the closure of the aortic valve, i.e. the second heart sound S2. From these detected characteristic features, the PLVDT metric can be calculated. The heart sound microphone can be placed inside the device (as will be illustrated in FIG. 5 and discussed below with reference to FIG. 5) or inside a specially adapted lead. In FIG. 2, a typical EKG waveform and heart sound waveforms at different frequencies are schematically illustrated. The PLVDT metric can be calculated using the identified heart sounds S1 (corresponding to the closure of the mitral and tricuspid valves) and S2 (corresponding to the closure of the aortic valve). Specifically, the PLVDT metric can be calculated according to the following:

$$PLVDT=100\times(A/RR),$$

where A is the diastolic time and RR the total heart cycle time.

Figure 3:
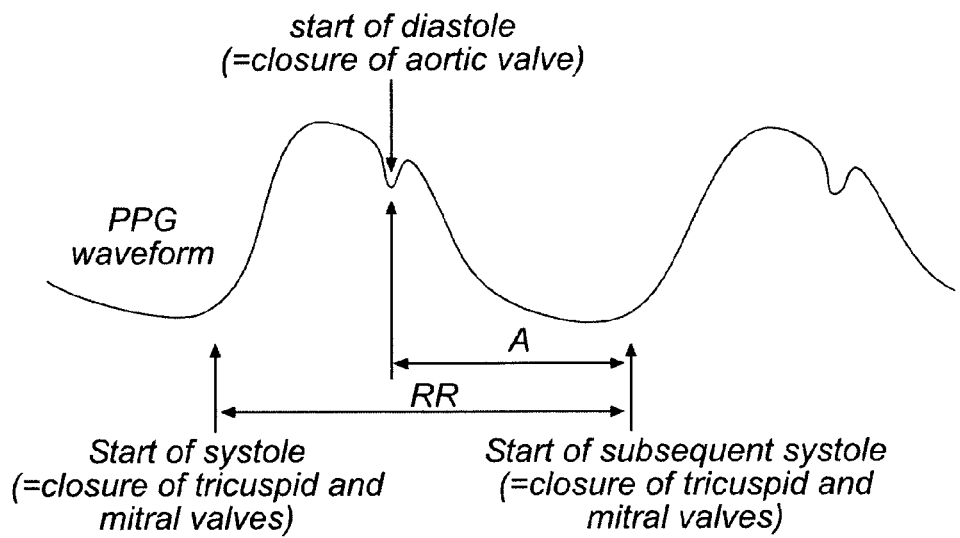
FIG. 3 schematically illustrates a photoplethysmographic waveform, where the time of mitral and tricuspid valves is marked and the closure of the aortic valve is marked.

According to another embodiment of the present invention, the PLVDT metric is calculated using data obtained by means of a photoplethysmograph (PPG) (as will be illustrated in FIG. 8 and discussed below with reference to FIG. 8). A light emitting device emits light into blood and the colour is measured by means of a light sensor. As arterial and venous blood have different colours, a pulsatile waveform is acquired which reflects the heart's pumping activity. By studying the PPG waveform, the time point of the closure of the mitral and tricuspid valves and the closure of the aortic valve, respectively, can be identified. In FIG. 3, a typical PPG waveform is schematically illustrated. The time point of the closure of the mitral and tricuspid valves can be identified as well as the time point of the closure of the aortic valve. Thereby, the start of the systolic and diastolic phase, respectively, can be identified. Using the identified time points of the valve closures, the PLVDT metric can be calculated. Specifically, the PLVDT metric can be calculated according to the following:

$$PLVDT=100\times(A/RR),$$

where A is the diastolic time and RR the total heart cycle time.

Figure 4:
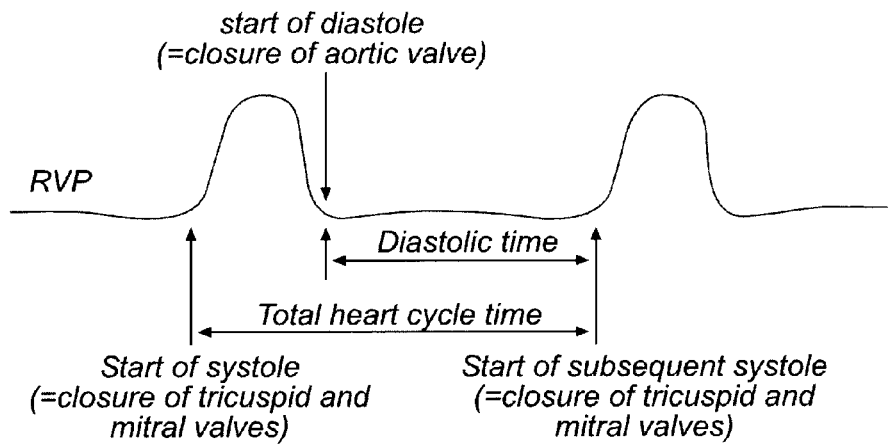
FIG. 4 schematically illustrates a intracardiac pressure waveform measured from inside the RV, where the time of mitral and tricuspid valves is marked and the closure of the aortic valve is marked.

In a further embodiment of the present invention, the IMD 8 includes an intracardiac pressure sensor (as will be illustrated in FIG. 7 and discussed below with reference to FIG. 7). The intracardiac pressure sensor may be placed in the RV, e.g. integrated in the lead 12, or in the LV, e.g. integrated in the lead 14. A pressure sensor in the RV would generate a pressure waveform as schematically illustrated in FIG. 4. As can be seen, the time point of the opening and closure of the mitral and tricuspid valves and the aortic valve, respectively, can be readily detected. The PLVDT metric can be calculated in a corresponding manner as described above.

According to yet another embodiment of the present invention, the IMD 8 includes an impedance measuring module (as will be illustrated in FIG. 9 and discussed below with reference to FIG. 9). The intracardiac impedance can be measured by means of a number of different electrode configurations, for example, between RA and LV using, for example, the electrode 28 located in right RA and the electrodes 21 and/or 23 located in the LV in a bi- or tri-polar configuration. The intracardiac impedance may be correlated with IEGM measurements to identify the time point of the opening and closure of the mitral and tricuspid valves and the aortic valve, respectively. Then, the PLVDT metric can be calculated in a corresponding manner as described above.

Figure 5:
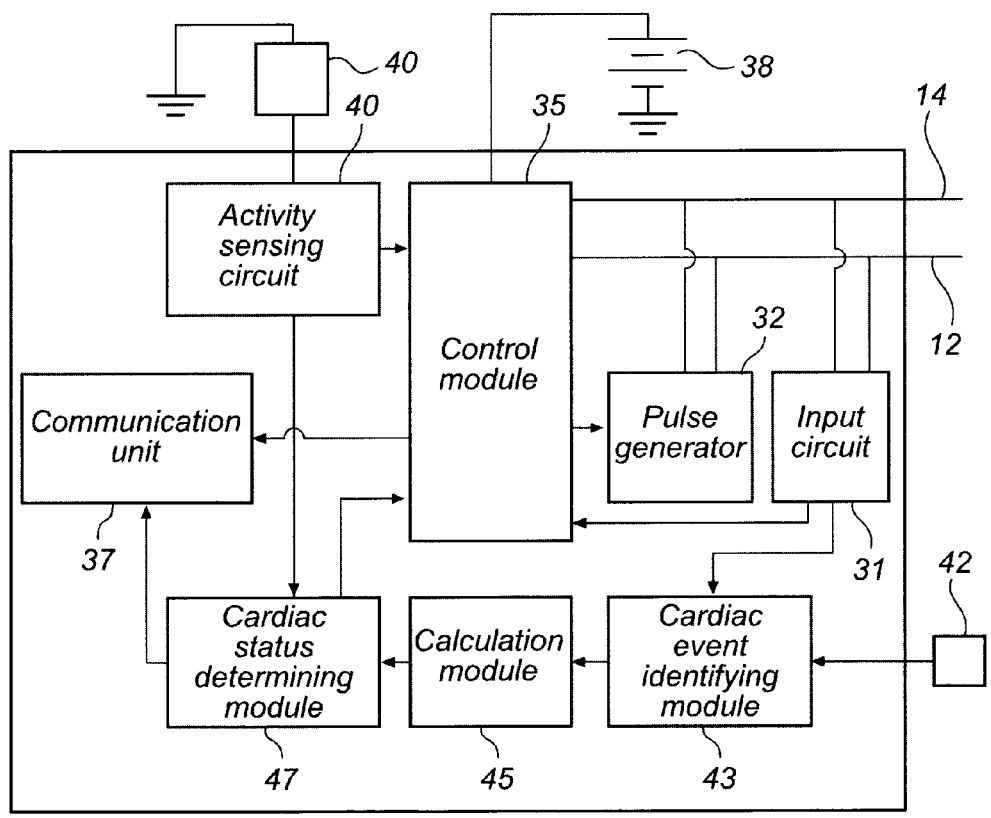
FIG. 5 is a functional block diagram form of the implantable medical device shown in FIG. 1, illustrating basic circuit elements that provide, for example, pacing stimulation in the heart and particularly illustrating components for calculating PLVDT (or PLVST) and for determining a cardiac status according to the present invention.

FIG. 5 is a block diagram illustrating the constituent components of an IMD 8 in accordance with one embodiment of the present invention. In the following, a number of different embodiments of the present invention will be discussed and similar or like part, components, modules, or circuits through the different embodiments will only be described with reference to FIG. 5. Hence, in the description of the further embodiments, the description of the similar or like part, components, modules, or circuits through the different embodiments will be omitted.

The IMD 8 is a pacemaker having a microprocessor based architecture. The IMD 8 includes an activity sensor or accelerometer 40 (e.g. a piezoceramic accelerometer), which preferably a sensor output that varies as a function a measured parameter relating the physical activity and/or metabolic requirements of the patient.

Further, the IMD includes a heart sound microphone 42 for detection of heart sounds including first and second heart sounds S1 and S2, respectively, for calculation of the PLVDT metric and to produce a heart sound amplitude signal. In one embodiment, the microphone is arranged in a lead and placed in or on epicardium. In US Pat. Appl. No. 2008/0091239 to Johansson et al. an example of a suitable microphone for implantation in or on epicardium is disclosed, which hereby is incorporated by reference herein in its entirety. It is also conceivable to arrange a microphone within the IMD 8, as disclosed in U.S. Pat. No. 6,064,910 to Andersson et al., which hereby is incorporated by reference herein in its entirety.

However, as an alternative or complement, the activity sensor 40 may detect heart sounds including first and second heart sounds S1 and S2, respectively, for calculation of the PLVDT metric.

The leads 12 and 14 comprises, as have been illustrated in FIG. 1, one or more electrodes, such a coils, tip electrodes or ring electrodes. These electrodes are arranged to, inter alia, transmit pacing pulses for causing depolarization of cardiac tissue adjacent to the electrode(-s) generated by a pace pulse generator 32 under influence of a control module or microcontroller 35. The rate of the heart 5 is controlled by software-implemented algorithms stored within a microcomputer circuit of the control module 35. The microcomputer circuit may include a microprocessor, a system clock circuit and memory circuits including random access memory (RAM) and read-only memory (ROM). The microcomputer circuit may further include logic and timing circuitry, state machine circuitry, and I/O circuitry. Typically, the control module 35 includes the ability to process or monitor input signals (data) from an input circuit 31 as controlled by a program code stored in a designated block of memory. The details and design of the control module 35 are not critical to the present invention. Rather, any suitable control module or microcontroller 35 may be used that carries out the functions described herein. The use of micro-processor-based control circuits for performing timing and data analysis functions are well known in the art.

Detected signals from the patient's heart 5, e.g. signals indicative of natural and stimulated contractions of the heart 5, are processed in an input circuit 31 and are forwarded to the microprocessor of the control module 35 for use in logic timing determination in known manner. The input circuit 31 may include, for example, an EGM amplifier for amplifying obtained cardiac electrogram signals.

IMD 8 comprises a communication unit 37 including an antenna (not shown), for example, a telemetry unit for uplink/downlink telemetry or RF transceiver adapted for bi-directional communication with external devices.

Electrical components shown in FIG. 5 are powered by an appropriate implantable battery power source 38 in accordance with common practice in the art. For the sake of clarity, the coupling of battery power to the various components of the IMD 8 is not shown in the figures.

Furthermore, with reference to FIG. 5, a cardiac event identifying module 43 is adapted to receive the heart sound amplitude signal from the microphone 42. A first heart sound, S1, is identified in the heart sound amplitude waveform, which corresponds to the closure of tricuspid and mitral valves. Further, the second heart sound, S2 is identified, which corresponds to the closure of the aortic valve. The cardiac event identifying module 43 calculates the diastolic period as the period of time from the occurrence of the second heart sound S2 of a cardiac cycle to the occurrence of the first heart sound S1 of the subsequent cardiac cycle and the cardiac cycle as the period of time from the occurrence of first heart sound S1 of a cardiac cycle to the occurrence of the first heart sound S1 of the subsequent cardiac cycle. In order to improve the identification of the heart sounds, the heart sound signal may be synchronized with an IEGM signal. For example, a time from a detected R-wave to the first and second heart sounds, respectively, can be calculated. This time should be substantially constant over time. It the time to respective heart sound are not substantially constant over time, this may be an indication that a detected heart sound in fact is caused by another extracardiac event. In such a case, the PLVDT calculation should be inhibited and then restarted.

A calculation module 45 is adapted to calculate the PLVDT metric using the identified heart sounds S1 (corresponding to the closure of the mitral and tricuspid valves) and S2 (corresponding to the closure of the aortic valve). Specifically, the PLVDT metric is calculated according to the following:

$$PLVDT=100 \times (A/RR),$$

where A is the diastolic time and RR the total heart cycle time. Alternatively, a PLVST metric can be calculated according to the following:

$$PLVST=100 \times ((RR-A)/RR).$$

A cardiac status determining module 47 is adapted to synchronize the activity level using the activity level signal received from the activity sensing circuit 40 with the calculated PLVDT (or PLVST) over time and to determine a cardiac status based on the calculated PLVDT (or PLVST) and on the activity level, wherein a gradually increasing or decreasing PLVDT (or PLVST) over time synchronized with a stable or gradually decreasing activity level is determined to be an indication of a impaired cardiac status. For example, a gradually increasing PLVDT (or decreasing PLVST) over time synchronized with a stable or gradually decreasing activity level is determined to be an indication of a impaired cardiac status. Similarly, a gradually decreasing PLVDT (or increasing PLVST) over time synchronized with a stable or gradually decreasing activity level may also be determined to be an indication of a impaired cardiac status. Consequently, a decreasing or increasing PLVDT (or PLVST) is an indication of an impairment of the cardiac status. However, the starting point must also be considered when determining the cardiac status as well as the activity level and/or heart rate. For example, a rather significant deviation (e.g. an increase or decrease) of the PLVDT (or PLVST) from a predetermined level or within a predetermined range at a specific activity level and/or heart rate for a specific patient may not be any indication (or a weak indication) of an imparied cardiac status, while a rather small deviation (e.g. an increase or decrease) from a predetermined level at a limit of the predetermined range for that specific patient may be a strong indication of an impaired cardiac status.

Figure 6:
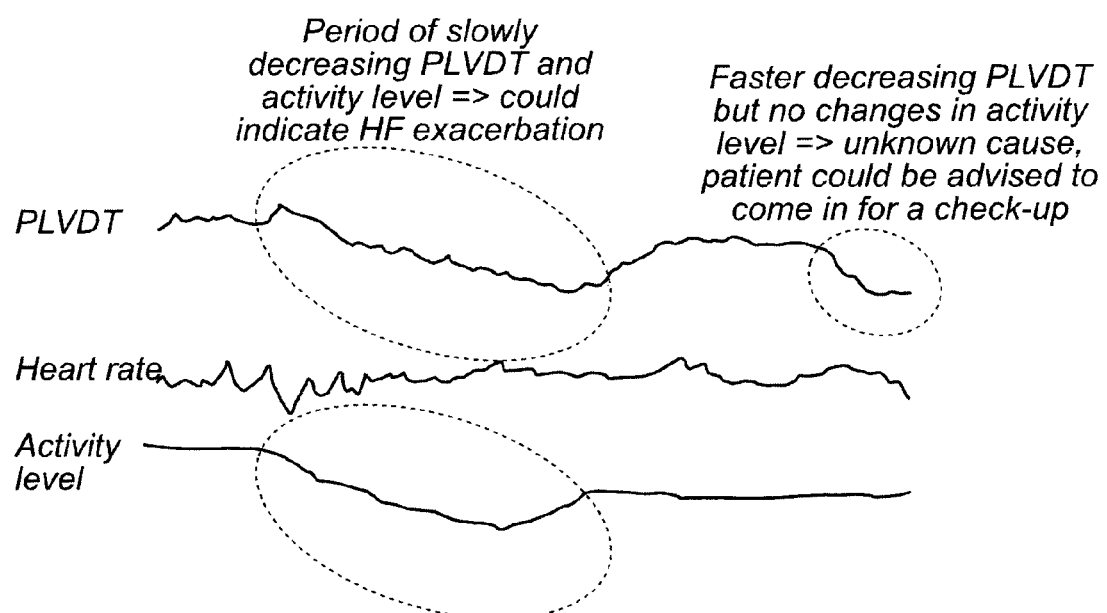
FIG. 6 schematically illustrates PLVDT synchronized with activity level and heart rate over time.

Studies have shown that a period of a gradually decreasing PLVDT correlated with a gradually decreasing activity level is an indication of an exacerbation of heart failure, see FIG. 6. This is an even stronger indication if the decreasing PLVDT is below a lower predetermined limit. It has been shown that a PLVDT may be between about 55%-65%, a range which however will vary between different patients and for different activity levels and/or heart rates. Further, a decreasing PLVDT correlated with a stable activity level is an indication of a potentially impaired cardiac status, and the patient may be given a notification advising him or her to visit the care provider for a check-up.

Thus, since the heart is unable to perfuse itself at a too short diastole, i.e. a too low PLVDT, the risk of ischemia increases as PLVDT decreases. Furthermore, an increased ventricular asynchrony would lead to a decrease in PLVDT as well as to an exacerbation of the patient's heart failure. Also, since heart failure patients are unable to increase their stroke volume as much as healthy individuals and thereby increase their rate and cardiac output to a higher degree at even moderate exercise, and since ischemia (both silent and non-silent) often make their debut at physical activity, trending the PLVDT in combination with the output from the activity sensor provides very important information regarding the cardiac status of the patient. To even further improve the specificity and accuracy of the status determination, the heart rate may be synchronized with the activity level and PLVDT.

IMD 8 may store the PLVDT, activity level and heart rate output over time in its memory, for example, in the control module 35. This trend is used in the status determination and can also be transmitted via the communication unit 37 to, for example, a clinic to be viewed by the physician at the next follow-up.

The PLVDT (or PLVST), the activity level and/or the heart rate as a function of time displayed on a programmer can be a very useful diagnostic tool for the medical doctor when determining a cardiac status of a patient in accordance with the discussion above. For example, a regular follow-up visit by the patient, or at a visit by the patient caused by a impairment of the experienced state of health, the medical doctor can use PLVDT (or PLVST) displayed simultaneously with the activity level and the heart rate on a programmer to determine a cardiac status. Thus, by studying the displayed graphs over time of the PLVDT (or PLVST), activity level and/or the heart rate and the trends over time, the doctor can, for example, determine whether a patient suffering from heart failure is getting worse or not. For example, a period of slowly decreasing PLVDT synchronized with a slowly decreasing activity level may be an indication of an exacerbation of heart failure.

Furthermore, the IMD 8 may include an alarm function, which may initiate an alarm based on the PLVDT and/or the status determination. For example, if a PLVDT exceeding or being below a predetermined range, e.g. above or below a range of 55%-65%, has been observed for a period of time at certain activity level and/or heart rate, the IMD 8 may issue a warning to the patient instructing him or her to get in contact with the hospital or clinic. The warning may be a message to a home monitoring unit in the patient's home transmitted wirelessly from the IMD 8, or a vibration of a vibrating unit in the IMD. The warning may also, or instead, be transmitted to the clinic instructing the physician to get in contact with the patient. For example, clinical experience has shown that a too low PLVDT may in some cases predict future VF (ventricular fibrillation). Thus, at a very low PLVDT, it may be time critical to get the patient to the hospital.

Figure 7:
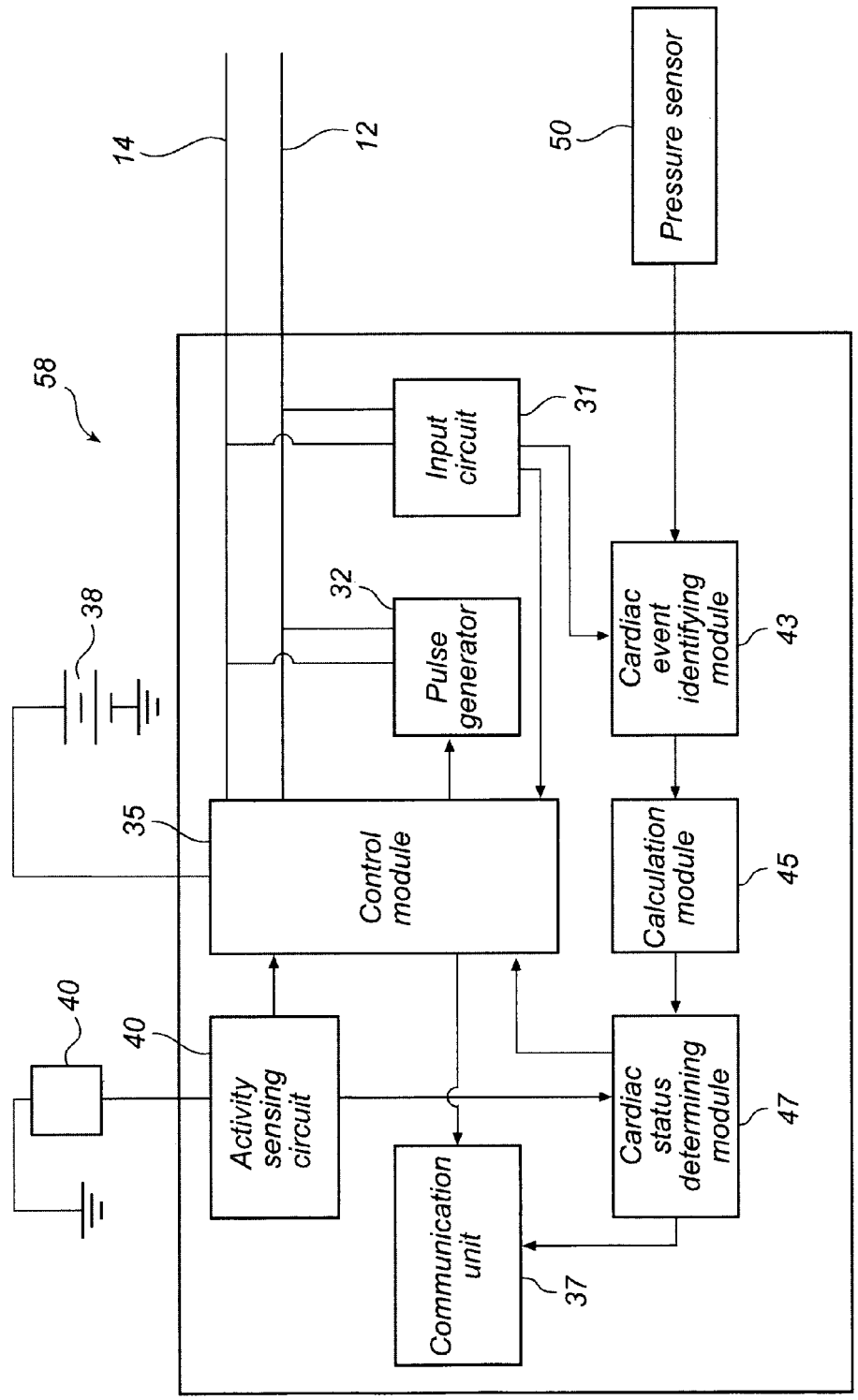
FIG. 7 is a functional block diagram form of another embodiment of an implantable medical device illustrating basic circuit elements that provide, for example, pacing stimulation in the heart and particularly illustrating components for calculating PLVDT (or PLVST) and for determining a cardiac status according to the present invention.

With reference now to FIG. 7, another embodiment of the present invention will be discussed. IMD 58 includes an intracardiac pressure sensor 50 adapted to produce a pressure amplitude signal. The pressure sensor 50 may be integrated in a lead 12, 14, or in a specialized lead and placed inside the RV or inside the LV. Other locations may be inside the aorta or in close contact with the LV. In U.S. Pat. No. 6,886,411 to Kjellman et al. a suitable pressure sensor is disclosed, which hereby is incorporated by reference herein in its entirety.

A pressure sensor in the RV would generate a pressure amplitude waveform as schematically illustrated in FIG. 4. As can be seen, the time point of the opening and closure of the mitral and tricuspid valves and the aortic valve, respectively, can be detected by the cardiac event identifying module 43. In particular, the cardiac event identifying module 43 is adapted to identify of a significant increase in a rate of change of pressure amplitude in the pressure amplitude waveform as the closure of tricuspid and mitral valves and a significant decrease of a rate of change of the pressure amplitude as the closure of the aortic valve. The diastolic interval and the cardiac cycle can be determined using the identified valve closures as indicated in FIG. 4, where the diastolic interval corresponds to the interval A and the cardiac cycle corresponds to the interval RR.

The calculation module 45 is adapted to calculate the PLVDT metric using the identified closure of the mitral and tricuspid valves and the closure of the aortic valve. Specifically, the PLVDT metric is calculated according to the following:

$$PLVDT=100\times(A/RR),$$

where A is the diastolic time and RR the total heart cycle time. Alternatively, a PLVST metric can be calculated according to the following:

$$PLVST=100\times((RR-A)/RR).$$

The cardiac status determining module 47 is adapted to synchronize the activity level using the activity level signal received from the activity sensing circuit 40 with the calculated. PLVDT (or PLVST) over time and, as described above, to determine a cardiac status based on the calculated PLVDT (or PLVST) and on the activity level.

Figure 8:
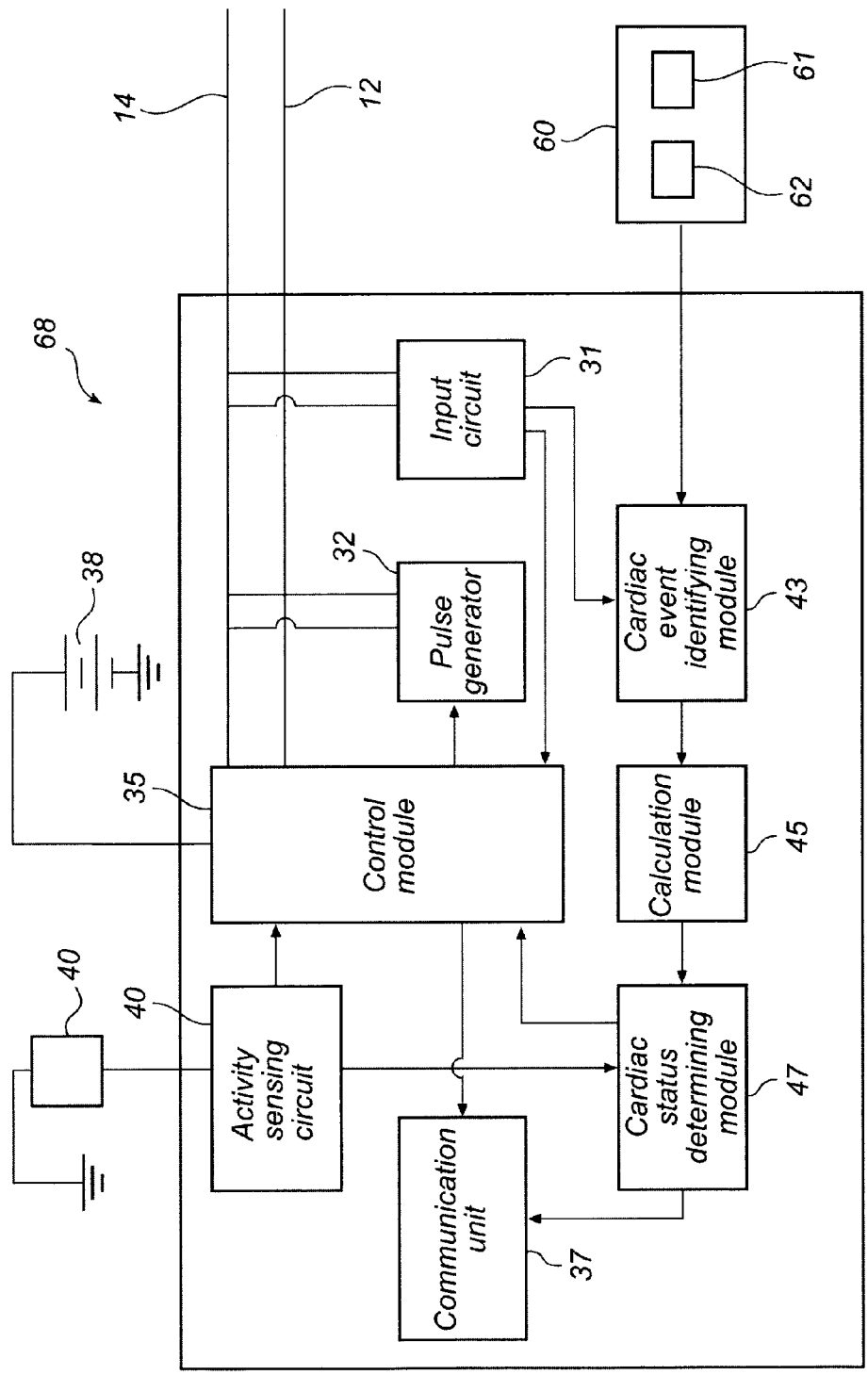
FIG. 8 is a functional block diagram form of a further embodiment of an implantable medical device illustrating basic circuit elements that provide, for example, pacing stimulation in the heart and particularly illustrating components for calculating PLVDT (or PLVST) and for determining a cardiac status according to the present invention.

Referring now to FIG. 8, another embodiment of the present invention will be discussed. IMD 68 includes an optical photoplethysmopraphic unit 60 comprising a light emitting circuit, for example, light emitting diodes (LED) 61 and a light receiving circuit 62, for example, a photo-detector. For example, the photoplethysmopraphic unit 60 may be incorporated into the IMD 68 and placed on the case of the IMD 68. Thereby, the blood flow in the surrounding pocked can be measured. The light emitting diodes 61 emit light into the blood stream and the light receiver measures the amount of received or transmitted light. The received light will be a measure of the amount of light absorbed by the blood and will essentially measure the colour of the blood. Arterial and venous blood have different colours and thereby a pulsatile waveform will be formed reflecting the heart's pumping activity. In FIG. 3 a schematic waveform of a light signal produced by a photoplethysmopraphic unit 60 is shown. In U.S. Pat. No. 7,447,533 to Fang et al. a suitable optical photoplethysmographic unit is disclosed, which hereby which hereby is incorporated by reference herein in its entirety.

The cardiac event identifying module 43 can identify the time point of the closure of the mitral and tricuspid valves as well as the time point of the closure of the aortic valve. In particular, a significant increase in a rate of change of the light absorption in a light absorption waveform obtained from the light receiving circuit 62 is identified as the closure of tricuspid and mitral valves and a first significant decrease in a rate of change of the light absorption is identified as a closure of the aortic valve. Further, a diastolic period, A, is determined as the period of time from the closure of the aortic valve of a cardiac cycle to the closure of tricuspid and mitral valves of the subsequent cardiac cycle and a cardiac cycle as the period of time from closure of tricuspid and mitral vales of a cardiac cycle to the closure of tricuspid and mitral valves of the subsequent cardiac cycle. Using the identified time points of the valve closures, the PLVDT metric can be calculated. Specifically, the PLVDT metric can be calculated according to the following:

$$PLVDT=100\times(A/RR),$$

where A is the diastolic time and RR the total heart cycle time. Alternatively, a PLVST metric can be calculated according to the following:

$$PLVST=100\times((RR-A)/RR).$$

The cardiac status determining module 47 is adapted to synchronize the activity level using the activity level signal received from the activity sensing circuit 40 with the calculated PLVDT (or PLVST) over time and, as described above, to determine a cardiac status based on the calculated PLVDT (or PLVST) and on the activity level.

Figure 9:
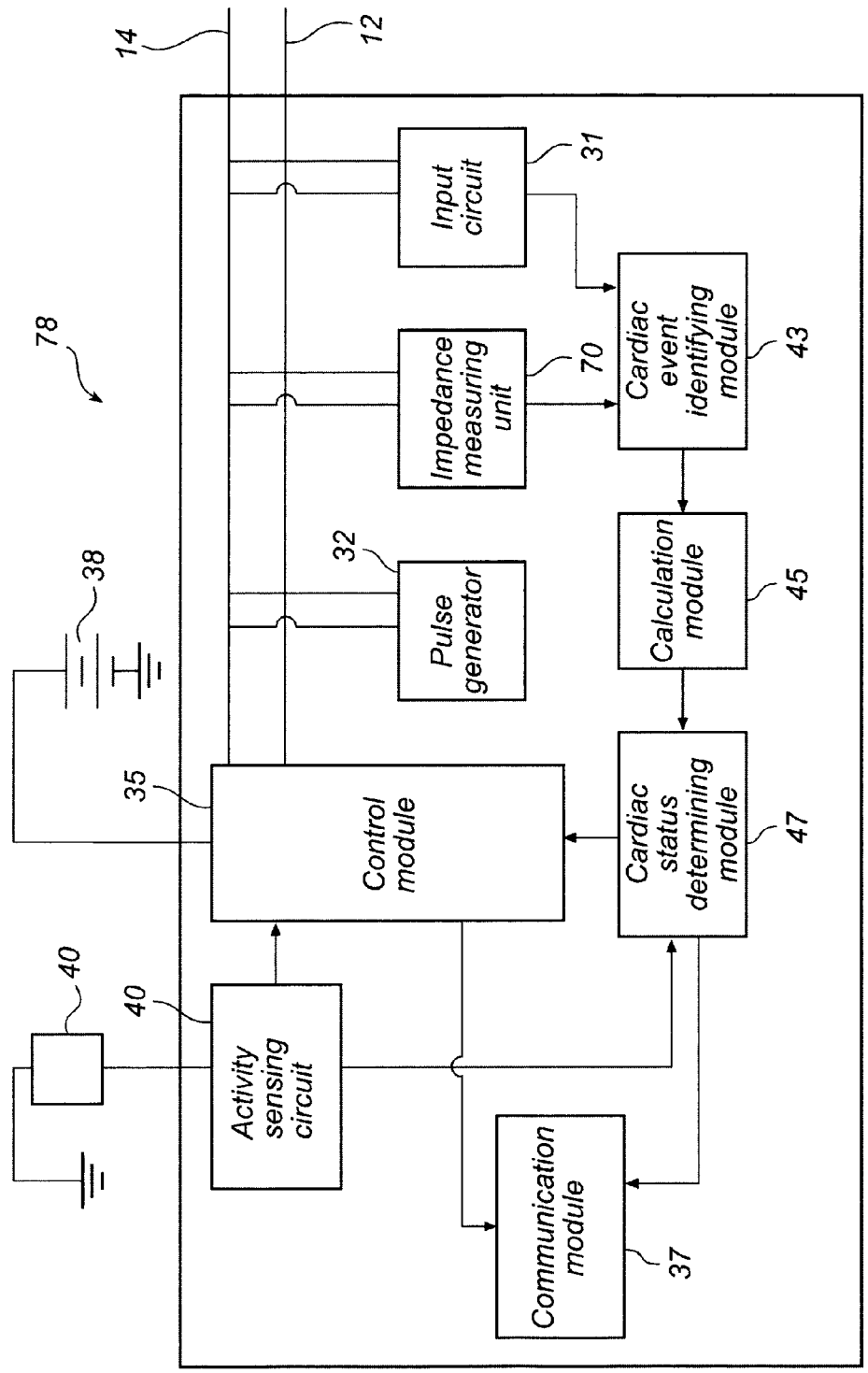
FIG. 9 is a functional block diagram form of another embodiment of an implantable medical device illustrating basic circuit elements that provide, for example, pacing stimulation in the heart and particularly illustrating components for calculating PLVDT (or PLVST) and for determining a cardiac status according to the present invention.

With reference now to FIG. 9, yet another embodiment of the present invention will be discussed. IMD 78 according to this embodiment includes an impedance measuring unit 70 adapted to carry out impedance measurements of the intracardiac impedance of the patient, for example, by means of applying a current over the RA electrode 28 (see FIG. 1) and the LV ring electrode 23 to measure impedance signals. The resulting voltage can, in a bi-polar configuration, be measured between the same electrodes. A tri- or quadro-polar configuration in RA and LV is also conceivable. Further configurations that have shown to provide accurate and useful impedance waveforms for identifying the closure of the mitral and tricuspid valves and the aortic valve, respectively, include RV and LV (e.g. using electrodes 22, 24, and/or 26, 23, and/or 21) in a bi-, tri-, or quadro-polar configuration, and LV (e.g. using electrodes 21 and 23) in a bi-polar configuration. The raw impedance data is then processed. To this end, the impedance measuring unit 70 may comprise, for example, amplifiers and filters e.g. FIR or IIR filters. Further, for example, amplitude normalizing and synchronization of the measured impedance sets in relation to a predetermined cardiac event may be performed.

In the cardiac event identifying module 43, the time point of the closure of the mitral and tricuspid valves as well as the time point of the closure of the aortic valve are identified in the impedance waveform. In a preferred embodiment, a reference impedance waveform for the patient has been recorded in which characteristic events such as the time point of the closure of the mitral and tricuspid valves as well as the time point of the closure of the aortic valve have been identified. Hence, by comparison with this reference waveform, the time point of the closure of the mitral and tricuspid valves as well as the time point of the closure of the aortic valve can be identified in a newly recorded impedance waveform. Then, the PLVDT or PLVST can be determined in the calculation module 45 in accordance with the description given above, and a cardiac status can be determined in the cardiac status determination module 47.

Figure 10:
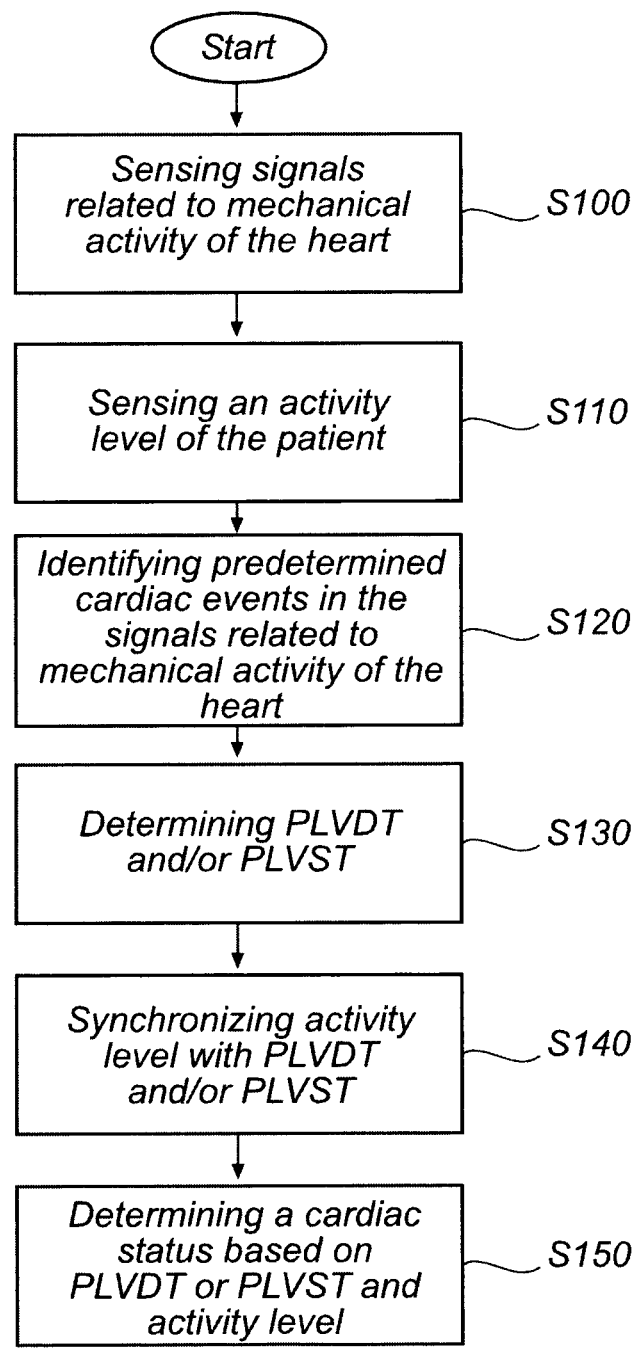
FIG. 10 schematically illustrates the general steps performed in the method for determining a cardiac status according to the present invention.

With reference to FIG. 10, the overall principles of a method according to the present invention will be discussed. First, in step S100, signals related to mechanical activity of the heart are sensed and output signals related to the mechanical activity are produced. As discussed above, a number of different signals may be sensed and used including intracardiac pressure, intracardiac impedance, heart sound, and photoplethysmographic signals. At step S110, an activity level of the patient is sensed. It should be noted that step S100 and S110 can be performed in reversed order or simultaneously. Thereafter, at step S120, predetermined cardiac events in the cardiac signals are identified and a systolic time interval and a diastolic time interval of a cardiac cycle using the identified cardiac events is determined. Preferably, the time points of the closure of the mitral and tricuspid valves and the closure of the aortic valve are identified. Then, at step S130, a percentage of left ventricular diastolic time (PLVDT) for a cardiac cycle corresponding to a relation between a diastolic time interval and a cardiac cycle time interval using the determined systolic and diastolic time intervals or a percentage of left ventricular systolic time (PLVST) for a cardiac cycle corresponding to a relation between a systolic interval time interval and a cardiac cycle time interval using the determined systolic and diastolic time intervals are calculated. At step S140, the activity level is synchronized with the calculated PLVDT (or PLVST) over time. Further, at step S150, a cardiac status based on the calculated PLVDT (or PLVST) and on the activity level is determined. It has, for example, been found by the inventors that a gradually increasing or decreasing PLVDT (or PLVST) over time synchronized with a stable or gradually decreasing activity level is determined to be an indication of a impaired cardiac status.

The PLVDT (or PLVST) may also be used for optimization of an implantable medical device (IMD) such as a pacemaker. It has been shown that a range for PLVDT may be about 55%-65%, and this may be used to control of pacing parameters of the IMD, for example, AV delay, W delay, rate response settings (slope, decay, rate responsive AV delay) or pacing configuration. Since the heart is perfused during diastole, a too small PLVDT would mean that the time for the heart muscle to perfuse itself is too short and hence the heart does not receive enough of the oxygen needed. An optimization procedure may include the following steps:

1. Measure PLVDT for a set of parameter settings—PLVDT1
2. Perform a parameter setting adjustment—a new set of parameter settings
3. Measure PLVDT for the new set of parameter settings—PLVDT2
   a. If PLVDT2 is better than PLVDT1, i.e. closer to a reference PLVDT within the range 55%-65%, the steps 1 and 2 are repeated.
   b. If PLVDT1 is better than PLVDT2, the parameter settings are adjusted in another way.
   c. If PLVDT1 is identical to PLVDT2 (or within a small range about PLVDT2), the optimization procedure is interrupted.

It should be stressed, that this optimization procedure is merely an example and should not be viewed as limiting the scope of the present invention. The optimization can be performed in the hospital, e.g. at follow-up, or automatically by the IMD. An automatic optimization can be made at regular time intervals (e.g. every 8 hours, once a day, once a week, etc.) or it may be triggered by a predetermined event (e.g. PLVDT exceeds or falls below a predetermined upper or lower limit, respectively, a change in heart failure status), etc.

If the optimization is performed in an in-clinic setting, the interacting physician or nurse may control the manner in which the parameter settings are adjusted and/or the initial parameter setting.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting.

The invention claimed is:

1. An implantable medical device for determining a cardiac status of a patient, said medical device being connectable to at least one medical lead for contact with tissue of a heart of said patient, said device comprising:

a sensor arrangement adapted to sense cardiac signals related to mechanical activity of said heart and to produce an output signal related to the mechanical activity;

an activity level sensor arrangement adapted to sense an activity level of said patient;

a cardiac event identifying module adapted to identify predetermined cardiac events in the cardiac signals and to determine a systolic time interval and a diastolic time interval of a cardiac cycle using said identified cardiac events;

a calculation module adapted to calculate a percentage of left ventricular diastolic time (PLVDT) for a cardiac cycle corresponding to a relation between a diastolic time interval and a cardiac cycle time interval using said determined systolic and diastolic time intervals or a percentage of left ventricular systolic time (PLVST) for a cardiac cycle corresponding to a relation between a systolic interval time interval and a cardiac cycle time interval using said determined systolic and diastolic time intervals, wherein said calculation module is adapted to determine a rate of change of said PLVDT (or PLVST) and said activity level; and a cardiac status determining module adapted to synchronize the activity level with said calculated PLVDT (or PLVST) over time and to determine a cardiac status based on said calculated PLVDT (or PLVST) and on said activity level and on a rate of change of said PLVDT (or PLVST) and on a rate of change of said activity level;

wherein PLVDT=LVDT/(LVDT+LVST) and PLVST=LVST/(LVDT+LVST);

wherein said sensor arrangement includes a light sensing module adapted to emit light into an artery or on vascular tissue and to receive light reflected in blood or transmitted in blood, said light sensing module being adapted to produce a signal corresponding to a light absorption of said blood over time.

2. The implantable medical device according to claim 1, wherein said sensor arrangement includes a heart rate sensor adapted to sense a heart rate of said patient; and wherein said cardiac status determining module is adapted to synchronize said heart rate with said PLVDT (or PLVST) over time and to determine a cardiac status based also on a development of the heart rate over time.

3. The implantable medical device according to claim 1, wherein said calculation module is adapted to determine a stable PLVDT (or PLVST) over time within a predetermined range defined by an upper and a lower limit to be an indication of a normal cardiac status and wherein a PLVDT (or PLVST) being outside said predetermined range at least a predetermined period of time is determined to be an indication of an impaired cardiac status.

4. The implantable medical device according to claim 3, wherein said cardiac status determining module is adapted to determine wherein a gradually increasing or decreasing PLVDT (or PLVST) over time synchronized with a stable or gradually decreasing activity level is determined to be an indication of a impaired cardiac status.

5. The implantable medical device according to claim 1, wherein said cardiac event identifying module is adapted to
identify a significant increase in a rate of change of said light absorption in a light absorption waveform obtained from said light sensing module as the closure of tricuspid and mitral valves and to identify a local minima of said light absorption as a closure of the aortic valve, and to
determine said diastolic period as the period of time from the closure of the aortic valve of a cardiac cycle to the closure of tricuspid and mitral valves of the subsequent cardiac cycle and a cardiac cycle as the period of time from closure of tricuspid and mitral vales of a cardiac cycle to the closure of tricuspid and mitral valves of the subsequent cardiac cycle.

6. An implantable medical device for determining a cardiac status of a patient, said medical device being connectable to at least one medical lead for contact with tissue of a heart of said patient, said device comprising:
a sensor arrangement adapted to sense cardiac signals related to mechanical activity of said heart and to produce an output signal related to the mechanical activity;
an activity level sensor arrangement adapted to sense an activity level of said patient;
a cardiac event identifying module adapted to identify predetermined cardiac events in the cardiac signals and to determine a systolic time interval and a diastolic time interval of a cardiac cycle using said identified cardiac events;
a calculation module adapted to calculate a percentage of left ventricular diastolic time (PLVDT) for a cardiac cycle corresponding to a relation between a diastolic time interval and a cardiac cycle time interval using said determined systolic and diastolic time intervals or a percentage of left ventricular systolic time (PLVST) for a cardiac cycle corresponding to a relation between a systolic interval time interval and a cardiac cycle time interval using said determined systolic and diastolic time intervals, wherein said calculation module is adapted to determine a rate of change of said PLVDT (or PLVST) and said activity level; and
a cardiac status determining module adapted to synchronize the activity level with said calculated PLVDT (or PLVST) over time and to determine a cardiac status based on said calculated PLVDT (or PLVST) and on said activity level and on a rate of change of said PLVDT (or PLVST) and on a rate of change of said activity level;

wherein PLVDT=LVDT/(LVDT+LVST) and PLVST=LVST/(LVDT+LVST);

wherein said sensor arrangement includes a heart sound detecting device adapted to detect heart sounds and to produce a signal corresponding to an amplitude of said detected heart sounds over time.

7. The implantable medical device according to claim 6, wherein said cardiac event identifying module is adapted to
identify the first heart sound, S1, as the closure of tricuspid and mitral valves in a heart sound amplitude waveform and the second heart sound, S2 as the closure of the aortic valve as; and to
determine said diastolic period as the period of time from the occurrence of the second heart sound of a cardiac cycle to the occurrence of the first heart sound of the subsequent cardiac cycle and a cardiac cycle as the period of time from the occurrence of first heart sound of a cardiac cycle to the occurrence of the first heart sound of the subsequent cardiac cycle.

8. An implantable medical device for determining a cardiac status of a patient, said medical device being connectable to at least one medical lead for contact with tissue of a heart of said patient, said device comprising:
a sensor arrangement adapted to sense cardiac signals related to mechanical activity of said heart and to produce an output signal related to the mechanical activity;
an activity level sensor arrangement adapted to sense an activity level of said patient;
a cardiac event identifying module adapted to identify predetermined cardiac events in the cardiac signals and to determine a systolic time interval and a diastolic time interval of a cardiac cycle using said identified cardiac events;
a calculation module adapted to calculate a percentage of left ventricular diastolic time (PLVDT) for a cardiac cycle corresponding to a relation between a diastolic time interval and a cardiac cycle time interval using said determined systolic and diastolic time intervals or a percentage of left ventricular systolic time (PLVST) for a cardiac cycle corresponding to a relation between a systolic interval time interval and a cardiac cycle time interval using said determined systolic and diastolic time intervals, wherein said calculation module is adapted to determine a rate of change of said PLVDT (or PLVST) and said activity level; and
a cardiac status determining module adapted to synchronize the activity level with said calculated PLVDT (or PLVST) over time and to determine a cardiac status based on said calculated PLVDT (or PLVST) and on said activity level and on a rate of change of said PLVDT (or PLVST) and on a rate of change of said activity level;

wherein PLVDT=LVDT/(LVDT+LVST) and
PLVST=LVST/(LVDT+LVST);

wherein said sensor arrangement includes an IEGM device adapted to sense electrical signals of said heart and to produce an IEGM signal; and wherein said cardiac event identifying module is adapted to synchronize said IEGM signal with heart sound amplitude signals, and to use an identification of a cardiac event in the IEGM signal to identify first and second heart sounds.

\* \* \* \* \*